(12) United States Patent
Li et al.

(10) Patent No.: US 9,089,446 B2
(45) Date of Patent: Jul. 28, 2015

(54) CORONARY ARTERY VASCULAR STENT WITH MEDICINE CARRYING SLOTS

(75) Inventors: Yan Li, Shanghai (CN); Changchun Wang, Shanghai (CN); Jianjun Li, Shanghai (CN); Zhiyong Xie, Shanghai (CN); Zhirong Tang, Shanghai (CN); Qiyi Luo, Shanghai (CN)

(73) Assignee: SHANGHAI MICROPORT MEDICAL (GROUP) CO., LTD., Pudong New Area, Shanghai (CN)

( * ) Notice: Subject to any disclaimer, the term of this patent is extended or adjusted under 35 U.S.C. 154(b) by 0 days.

(21) Appl. No.: 13/127,548

(22) PCT Filed: Nov. 2, 2009

(86) PCT No.: PCT/CN2009/074754
§ 371 (c)(1),
(2), (4) Date: May 4, 2011

(87) PCT Pub. No.: WO2010/051740
PCT Pub. Date: May 14, 2010

(65) Prior Publication Data
US 2011/0238157 A1     Sep. 29, 2011

(30) Foreign Application Priority Data

Nov. 4, 2008 (CN) .......................... 2008 1 0202191

(51) Int. Cl.
| | |
|---|---|
| *A61F 2/06* | (2013.01) |
| *A61F 2/88* | (2006.01) |
| *A61F 2/82* | (2013.01) |
| *A61F 2/915* | (2013.01) |
| *A61F 2/91* | (2013.01) |

(52) U.S. Cl.
CPC . *A61F 2/915* (2013.01); *A61F 2/91* (2013.01); *A61F 2002/91508* (2013.01); *A61F 2002/91558* (2013.01); *A61F 2230/0054* (2013.01); *A61F 2250/0068* (2013.01)

(58) Field of Classification Search
USPC .............................................. 623/1.42, 1.46
See application file for complete search history.

(56) References Cited

U.S. PATENT DOCUMENTS

| | | | | |
|---|---|---|---|---|
| 5,922,020 | A * | 7/1999 | Klein et al. ................. | 623/1.15 |
| 6,042,606 | A * | 3/2000 | Frantzen ...................... | 623/1.18 |
| 6,056,776 | A * | 5/2000 | Lau et al. ..................... | 623/1.16 |
| 6,129,755 | A * | 10/2000 | Mathis et al. ................ | 623/1.15 |

(Continued)

FOREIGN PATENT DOCUMENTS

| | | |
|---|---|---|
| CN | 2749469 Y | 1/2006 |
| CN | 201019862 Y | 2/2008 |
| WO | 2006/058479 A1 | 6/2006 |

OTHER PUBLICATIONS

PCT/CN2009/074754 International Search Report.

*Primary Examiner* — Thomas J Sweet
*Assistant Examiner* — Seema Mathew
(74) *Attorney, Agent, or Firm* — Michael Best & Friedrich LLP (57) ABSTRACT

The present invention discloses a coronary artery vascular stent with drug carrying slots (2), comprising a plurality of main supporting unit rings (1,8) and connecting rods (4,6). Said main supporting unit rings comprise a plurality of unit waves. There are drug carrying slots (2) at the outer surface of the rods of said unit waves, characterized in that the total slot length of the drug carrying slots (2) is 60%-75% of the total wave rod length of the main supporting unit rings (1,8).

14 Claims, 5 Drawing Sheets

(56) References Cited

U.S. PATENT DOCUMENTS

| | | | |
|---|---|---|---|
| 6,179,867 B1* | 1/2001 | Cox | 623/1.15 |
| 6,254,632 B1 | 7/2001 | Wu et al. | |
| 6,379,381 B1* | 4/2002 | Hossainy et al. | 623/1.42 |
| 6,506,437 B1* | 1/2003 | Harish et al. | 427/2.25 |
| 6,699,281 B2 | 3/2004 | Vallana et al. | |
| 6,758,859 B1* | 7/2004 | Dang et al. | 623/1.15 |
| 7,056,339 B2 | 6/2006 | Elkins et al. | |
| 7,135,038 B1* | 11/2006 | Limon | 623/1.15 |
| 7,163,555 B2* | 1/2007 | Dinh | 623/1.42 |
| 7,169,178 B1* | 1/2007 | Santos et al. | 623/1.42 |
| 7,722,661 B2* | 5/2010 | Lenz et al. | 623/1.15 |
| 7,763,066 B2* | 7/2010 | Parker | 623/1.15 |
| 7,951,192 B2* | 5/2011 | Yadin et al. | 623/1.35 |
| 8,333,801 B2* | 12/2012 | Bienvenu | 623/1.42 |
| 8,353,950 B2* | 1/2013 | Shanley et al. | 623/1.22 |
| 8,439,968 B2* | 5/2013 | Shanley | 623/1.42 |
| 2001/0027339 A1* | 10/2001 | Boatman et al. | 623/1.15 |
| 2001/0032011 A1* | 10/2001 | Stanford | 623/1.15 |
| 2002/0068969 A1* | 6/2002 | Shanley et al. | 623/1.16 |
| 2003/0004564 A1* | 1/2003 | Elkins et al. | 623/1.15 |
| 2004/0034402 A1* | 2/2004 | Bales et al. | 623/1.2 |
| 2004/0093073 A1* | 5/2004 | Lowe et al. | 623/1.15 |
| 2004/0172123 A1* | 9/2004 | Lootz et al. | 623/1.15 |
| 2005/0278016 A1* | 12/2005 | Welsh et al. | 623/1.42 |
| 2007/0239263 A1* | 10/2007 | Fliedner | 623/1.16 |
| 2007/0265698 A1* | 11/2007 | Pienknagura | 623/1.16 |
| 2008/0183270 A1* | 7/2008 | Rea | 623/1.11 |
| 2009/0076591 A1* | 3/2009 | Girton et al. | 623/1.16 |
| 2009/0287295 A1* | 11/2009 | Contiliano et al. | 623/1.15 |
| 2010/0082096 A1* | 4/2010 | Gregorich | 623/1.43 |
| 2010/0152836 A1* | 6/2010 | De Scheerder et al. | 623/1.16 |
| 2010/0238153 A1* | 9/2010 | Sehata et al. | 345/211 |
| 2010/0249904 A1* | 9/2010 | Takayuki et al. | 623/1.16 |
| 2011/0054590 A1* | 3/2011 | Leopold et al. | 623/1.15 |
| 2011/0066227 A1* | 3/2011 | Meyer et al. | 623/1.42 |
| 2011/0070358 A1* | 3/2011 | Mauch et al. | 427/2.25 |
| 2011/0245904 A1* | 10/2011 | Pacetti et al. | 623/1.15 |
| 2012/0029622 A1* | 2/2012 | Baillargeon et al. | 623/1.16 |
| 2013/0131780 A1* | 5/2013 | Armstrong et al. | 623/1.13 |
| 2013/0261727 A1* | 10/2013 | Perkins et al. | 623/1.12 |
| 2015/0073535 A1* | 3/2015 | Consigny et al. | 623/1.38 |

* cited by examiner

Fig. 9

CORONARY ARTERY VASCULAR STENT WITH MEDICINE CARRYING SLOTS

CROSS-REFERENCE TO RELATED APPLICATIONS

This patent application is a national stage filing under 35 U.S.C. 371 of International Application No. PCT/CN2009/074754, filed Nov. 2, 2009, which claims foreign priority to Chinese Patent Application No. 200810202191.4, filed Nov. 4, 2008, the disclosures of which are incorporated by reference herein in their entireties. Priority to each application is hereby claimed.

TECHNICAL FIELD

The present invention pertains to the field of medical instruments, and it relates to a type of coronary vascular stent, especially a type of coronary artery vascular stent with drug-carrying slots.

BACKGROUND OF THE INVENTION

Sigwart succeeded in implementing the first surgery of coronary artery vascular stent in 1987. After that, coronary artery stent has been widely accepted as the second milestone in the history of interventional therapy of coronary heart diseases.

Common metallic stents are produced from 316L stainless steel, cobalt chromium alloy or nickel titanium alloy. Although these metallic stents meet the requirements of mechanical properties in the structure, they contact directly with blood after implanted into the human body, which stimulates the rejection capability of the human body to foreign matters, causing hyperplasia of the vascular intima tissue and the smooth muscle cells. Moreover, as the stent surface gets rougher, the possibility of cruor occurring gets larger. Metallic stents also release heavy metal ions under blood circulation, and these heavy metal ions would promote happening of thrombus. These factors lead to happening of restenosis after the stent implantation.

In this case, drug-eluting stents have been developed as required. The drug is coated onto the metallic stent through some processing, and after the stent is implanted into the body, the drug can be released at the region of lesion, maintaining a releasing period, which effectively prevents post-operative restenosis in-stent. However, most of the present drug stents are coated with drug on both the interior and exterior metallic surfaces, so as to render high drug concentration inside the blood vessel and high releasing rate, and the releasing direction cannot be controlled effectively, making some of the drug can not be absorbed by the blood vessel wall. Besides, at the places where the stent shape changes relatively largely, the coating herein will easily fall off during the process of stent propelling and expansion. The fallen drug mass flows with blood, and easily causes thrombus, leading to new damages.

So far there are already vascular stent with drug-carrying slots on the market, and the vascular stent normally has a net tube shaped structure, comprising a plurality of main structure struts with sinusoidal waveform structure. The adjacent main structure rods are connected there between with connecting rods, and the exterior surface of the main structure rod has drug-carrying slots. This vascular stent with drug-carrying slots can improve the distribution of the drug in the blood vessel, increase the adhesion capability of the coating on the stent, and prolong the functioning time of the drug. However, the length of the drug-carrying slots is very important. If the length is too short, it will cause nonhomogeneous distribution of the drug in the slots, and the drug loading cannot meet the requirements for effective cure of lesion; if the length is too long, it would surely affect the mechanical property of the stent, causing fracture of the stent.

SUMMARY OF THE INVENTION

Therefore, the first technical problem to be solved in the present invention is to provide a type of coronary vascular stent with drug-carrying slots, and in this type of vascular stent, the mechanical property of the stent would not be affected for having the drug-carrying slots.

The second technical problem to be solved in the present invention is to provide a type of coronary vascular stent with drug-carrying slots, and such vascular stent can increase the capture capability of the sample application system with respect to the center position of the slots, and increase the quality of the stent drug dripping.

The third technical problem to be solved in the present invention is to provide a type of coronary vascular stent with drug-carrying slots, and such vascular stent can increase the support force to the plaque of lesion.

These technical problems can be solved through the following technical solution: provide a type of coronary artery vascular stent with drug-carrying slots, which is comprised of a plurality of main supporting unit rings and connecting rods at the near-end, far-end and in the intermediate portions of the stent, the main supporting unit ring consists of a plurality of unit waves, the wave rod exterior surface of which has drug-carrying slots, characterized in that the accumulative slot-length of the drug-carrying slots covers 60%-75% of the wave rod length of the main supporting unit rings.

Preferably, the accumulative slot-length of the drug-carrying slots covers 64%-70% of the wave rod length of the main supporting unit rings.

According to the present invention, if the accumulative slot-length of the drug-carrying slots covers more than 75% of the wave rod length of the main supporting unit rings, fracture phenomenon would happen in the vascular stent in the limit expansion fracture experiment and fatigue test; if the accumulative slot-length of the drug-carrying slots covers less than 60% of the wave rod length of the main supporting unit rings, it causes nonhomogeneous distribution of the drug in the slots, and the drug-carrying amount cannot meet the requirements for effective cure of lesion.

The unit wave consists of a reinforcement ring, a straight rod segment and a transition segment connecting the reinforcement ring and the straight rod segment.

The straight rod segment and the transition segment are slightly wider than the reinforcement ring. Preferably, the straight rod segment and the transition segment are 5-15% wider than the reinforcement ring.

The unit waves at the near-end and the far-end of the stent render a "U" shape, and the connecting rods between the main supporting unit rings at the near-end and the far-end and the adjacent support unit rings are connected at the wave crests of two adjacent "U" shaped unit waves, rendering "crest to crest" connection.

The connecting rods at the near-end and the far-end of the stent are "n" shaped connecting rods.

The unit wave in the intermediate portion of the stent is comprised of two types of wave shapes, wherein the wave shape length of one type is obviously shorter than that of the other type. Preferably, the wave shape length of the one type is 25-35% shorter than that of the other type.

After the stent has been cut from the tubing, the intermediate portion of the stent can be considered to be comprised of "U" shaped wave and "W" shaped wave for the convenience of stent recognition. The connecting rods between the adjacent central main supporting wave rods are connected from the wave crest of the "U" shaped wave to the wave base of the "W" shaped wave, rendering "crest to base" connection.

The connecting rods in the intermediate portion of the stent are made by connecting the "S" shaped curved portion to the straight portion, wherein the straight portion is completely vertical to the longitudinal axis of the stent.

According to the present invention, the adjacent main supporting unit rings are connected by the connecting rods to form a cylinder-shaped circular stent.

According to the specific requirements, the drug-carrying slots are mainly located at the straight rod segment of the unit waves, or at the straight rod segment and the transition segment, or extend to a small segment of the reinforcement ring.

The reinforcement ring may be a circular arc with a radian larger than 180 degrees.

The wave rod exterior surface of each unit wave only has one drug-carrying slot.

The drug-carrying slots can be strip-shaped.

The drug-carrying slots can be a non-penetrable slots.

The width of the drug-carrying slots can be 45%-60% of the width of the unit wave straight rod segment.

The depth of the drug-carrying slots can be 15%-30% of the thickness of the stent.

The drug-carrying slots can be made by laser cutting technique.

The vascular stent is made of cobalt based alloy, stainless steel or magnesium alloy.

Compared to the current techniques, the vascular stent with drug-carrying slots in the present invention, besides those advantages of improving the drug distribution in the blood vessel, increasing the adhesion of the coating on the stent, and extending the functioning time of the drug, have the following advantages:

When the accumulative slot-length of the drug-carrying slots covers 60-75% of the wave rod length of the main supporting unit rings, the mechanical properties of the vascular stent with the drug-carrying slots is maintained well. If the drug-carrying slots are too long, the notching position would be extended excessively to the wave crest of the reinforcement ring. When the stent expands, as the expansion pressure increases, the notching portion of the reinforcement ring has smaller sectional area and larger stress than that of the non-notching portion, and fracture phenomenon happens at the interface between the notching and non-notching portions. If the slots cover the whole main supporting wave rod, it will make the stent become thinner and lead to corrosion fracture and fatigue fracture in the stent. Therefore, the reasonable design of the slot-length in the present invention not only reduces the risks of stent expansion fracture, but also increases its capabilities of resistance to corrosion and fatigue fracture.

In the unit waves constituting the stent main supporting wave rods of the present invention, because the straight rod segment and the transition segment are slightly wider than the reinforcement ring, in the case of a certain width of the slots, when dripping drug to the stent drug-carrying slots, on one hand, the catching capability of the sample application system with respect to the center position of the slots is increased, and on the other hand, when there is not enough time for the drug solvent to evaporate, the drug tends to overflow, at this time because the slots edge is relatively wide, the adhesion of the drug to the slots wall is increased, which avoids the drug to overflow to the interior and exterior surfaces and the side surface outside the stent slots, increasing the quality of the stent drug dripping.

The unit waves in the intermediate portion of the stent are comprised of two types of waves with different wave shape lengths, and a connecting rod is connected from the wave crest of a main supporting unit wave to the wave base of the adjacent main supporting unit wave, rendering "crest to base" connection, which makes the distance between the two adjacent main supporting unit rings become smaller, thereby decreases the mesh area of the stent, and increases the support to the plaque of lesion.

The special design of the stent connecting rod structure increases the flexibility of the stent, and the "n" shaped connecting rod at both ends of the stent has a certain elastic force, which can decrease the axial contracting; the connecting rod is made by connecting the "S" shaped curved segment to the straight segment, wherein the straight segment is vertical to the longitudinal axis of the stent, increasing the longitudinal flexibility of the stent. When the stent passes through bended blood vessel, the curved portion and the straight portion of the connecting rod would allow the stent to bend longitudinally, and the ability of the stent to cure lesion is highly increased.

DETAILED DESCRIPTION OF THE EMBODIMENTS

The specific embodiments of the present invention are described in combination with the drawings as follows.

Figure 1:
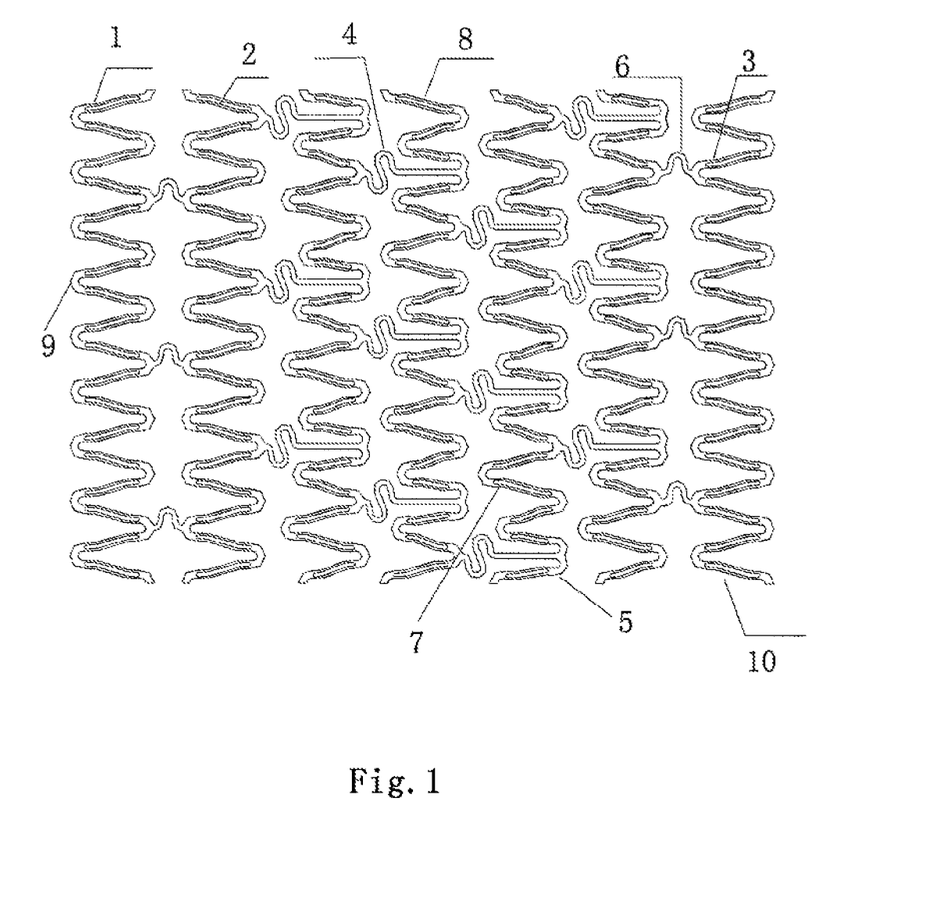
FIG. 1 is a schematic diagram of the planar structure of the stent expanded in the axial direction according to a first embodiment of the present invention.
Figure 2:
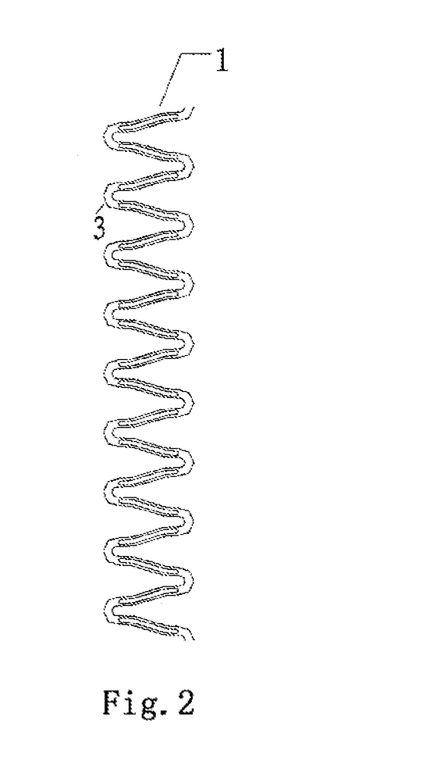
FIG. 2 is a structural schematic diagram of the near-end and the far-end main supporting unit rings in the stent according to the first embodiment of the present invention.
Figure 3:
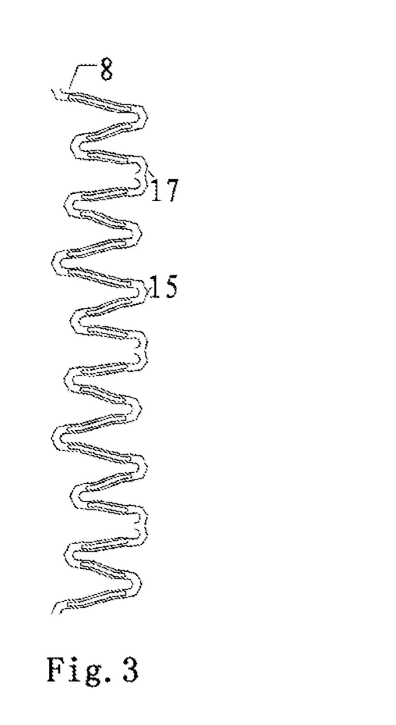
FIG. 3 is a structural schematic diagram of the main supporting unit rings in the intermediate portion in the stent according to the first embodiment of the present invention.
Figure 5:
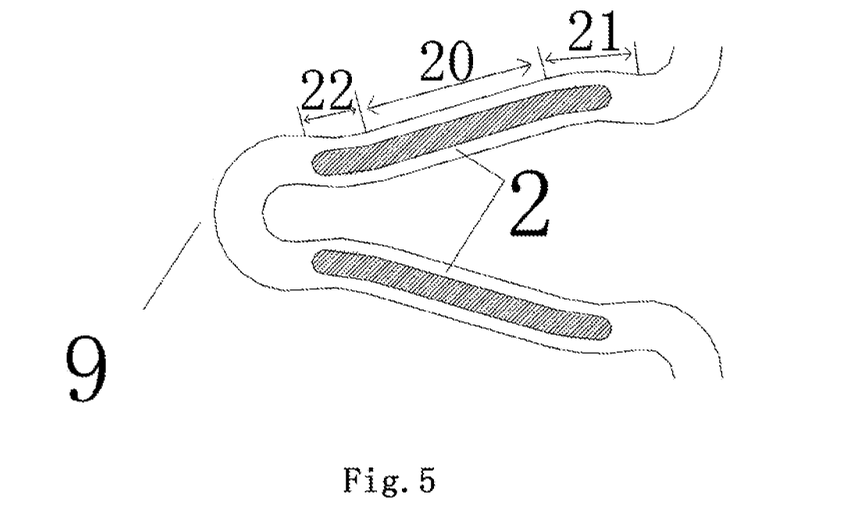
FIG. 5 is a partial structural schematic diagram of the notching position according to the first embodiment of the present invention.

In combination with that shown in FIG. 1, FIG. 2 and FIG. 3, the stent structure of a first embodiment is comprised of a plurality of main supporting unit rings 1, 8 and connecting rods 6, 4 that connect the unit rings, wherein the main supporting unit ring are comprised of a plurality of unit waves. As shown in FIG. 5, the unit wave is comprised of reinforcement ring 9 of the circular arc segment, straight rod segment 20 and the transition segments 21 and 22 connecting the reinforcement rings and the straight rod segment, and the exterior surface of the unit wave rod has drug-carrying slots 2 which can be loaded with drug.

Figure 4:
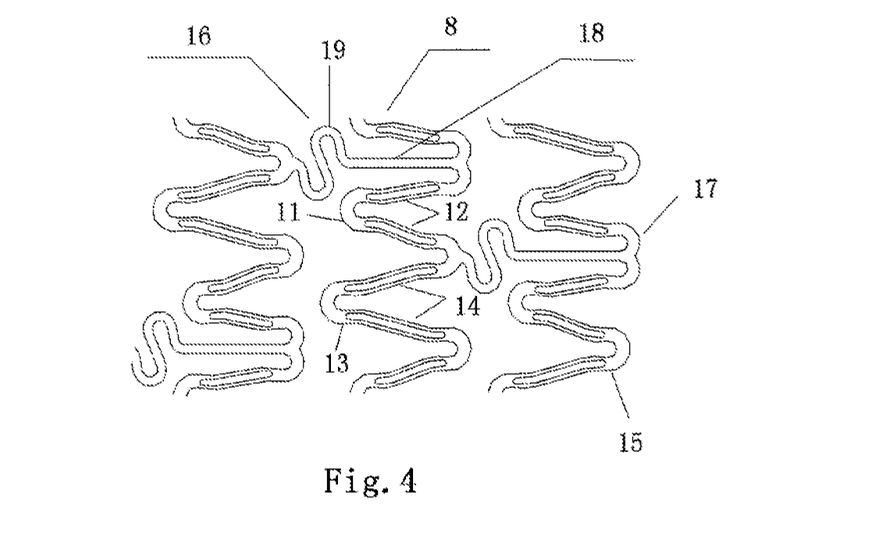
FIG. 4 is a partial structural schematic diagram of the intermediate portion in the stent according to the first embodiment of the present invention.

In the axial direction of the stent, the main supporting unit rings 1 and 10 at the near-end and the far-end are comprised of a plurality of "U" shaped waves 3, and the connecting rods between adjacent unit rings are "n" shaped connecting rods 6, which are connected at the wave crests of two adjacent "U" shaped unit waves, rendering "crest to crest" connection. As shown in FIG. 4, the main supporting unit rings 8 in the intermediate portion of the stent are comprised of two types of wave shapes, wherein the first type of wave shape 11 corresponds to the first type of supporting structure 12, while the second type of wave shape 13 corresponds to the second type of supporting structure 14, and the first type of wave shape has a length obviously shorter than that of the second type of wave shape. When the stent is under the grasping status, the two types of wave shapes would come closer to each other respectively. The intermediate portion of the stent can also be considered to be comprised of "U" shaped waves 15 and "W" shaped waves 17. The connecting rod 16 between the adjacent intermediate units are connected from the wave crest of the "U" shaped wave to the wave base of the "W" shaped wave, rendering "crest to base" connection. The connecting rod 16 is made by connecting a "S" shaped curved portion 19 to the straight portion 18, wherein the straight segment is completely vertical to the longitudinal axis of the stent.

The width of the straight rod segment in the unit wave of the main supporting unit ring in the first embodiment is 96 μm, and the width of the reinforcement ring is 91 μm, and the straight rod segment is slightly wider than the reinforcement ring by approximately 5%. The transition segment connects the straight rod segment and the reinforcement ring smoothly. In the intermediate portion of the stent, the first type of wave shape is 25% shorter than the second type of wave shape. The thickness of the stent is 100 μm, and the drug-carrying slots are cut out by laser cutting technique with a slots width of 55 μm and a depth of 30 μm, and the accumulative slot-length covers 60% of the total wave rod length of the main supporting unit rings. As shown in FIG. 5, drug-carrying slots 2 is located at the straight rod segment 20 and the transition segments 21, 22 of the stent main supporting unit wave rod, but the tops of the slots are not in contact with the edges of the transition segment.

Figure 6:
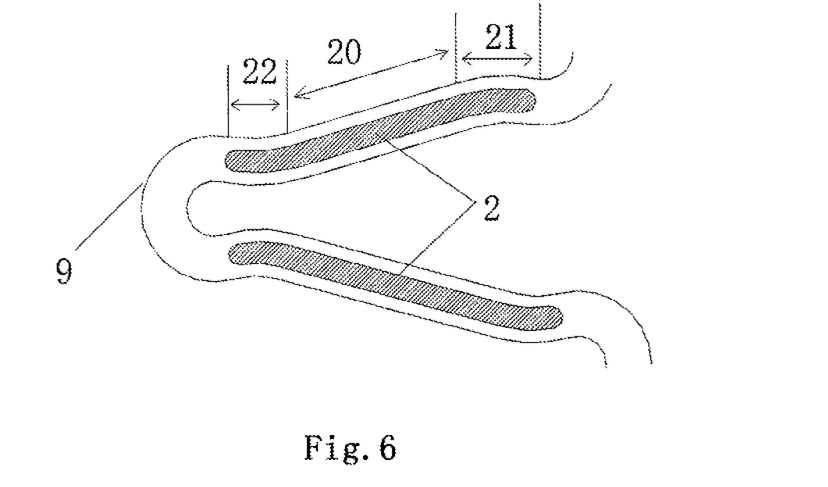
FIG. 6 is a partial structural schematic diagram of the notching position according to a second embodiment of the present invention.

The stent structural design, the width and thickness of the unit wave rod, the width and depth of the drug-carrying slots of the second embodiment are the same as those of the first embodiment, and the length and the position of the slots is shown in FIG. 6, and the accumulative slot-length covers 64% of the total wave rod length of the main supporting unit rings. The drug-carrying slots 2 are notched on the straight rod segment 20 and the transition segments 21, 22 of the stent main supporting wave rod, but there is not any slot on the reinforcement ring 9. The width of the straight rod segment and the reinforcement ring are the same as that of the first embodiment.

Figure 7:
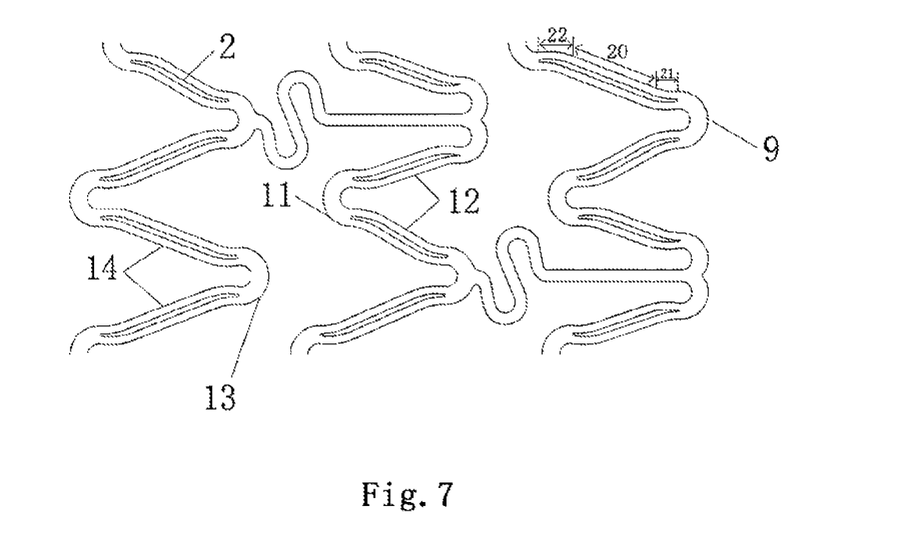
FIG. 7 is a partial structural schematic diagram of the intermediate portion in the stent according to a third embodiment of the present invention.

The stent structural design of the third embodiment is the same as that of the first embodiment, only with the difference of the size of the unit wave, and FIG. 7 is a partial structural schematic diagram of the intermediate portion. In the unit wave, the width of the straight rod segment is 107 μm, and the width of the reinforcement ring is still 91 μm, and the straight rod segment is 15% wider than the reinforcement ring. In the intermediate portion of the stent, the wave shape of the first type 11 is 35% shorter than the wave shape of the second type. The thickness of the stent is 100 μm, and the drug-carrying slots have a width of 55 μm and a depth of 25 μm. The accumulative slot-length is the same as the second embodiment, and it still covers 64% of the total wave rod length of the main supporting unit rings, and the notching position does not extend to the reinforcement ring 9.

Figure 8:
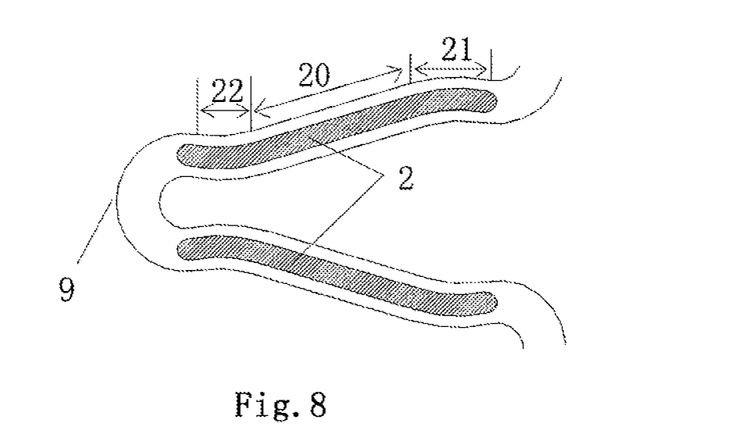
FIG. 8 is a partial structural schematic diagram of the notching position according to a fourth embodiment of the present invention.

The length and position of the slots in the fourth embodiment is shown in FIG. 8, and the drug-carrying slots 2 are located at the straight rod segment 20 and the transition segments 21, 22 of the stent main supporting wave rod, while extending to a small segment of the reinforcement ring, and the accumulative slot-length covers 70% of the total wave rod length of the main supporting unit rings. The stent structural design and size are the same as the first embodiment.

Figure 9:
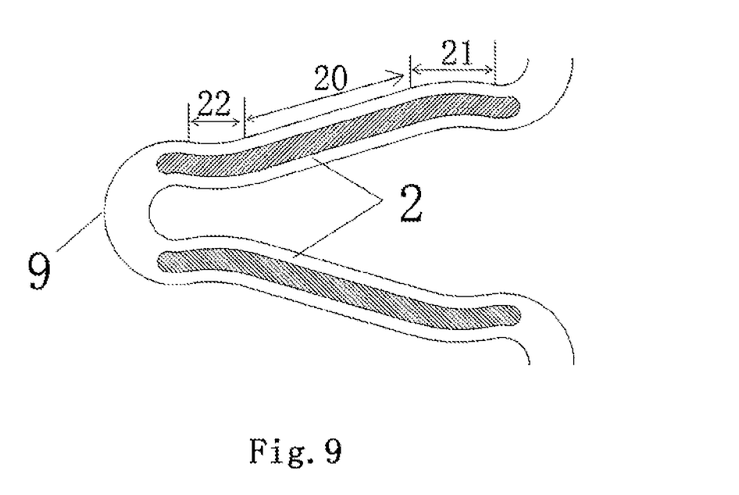
FIG. 9 is a partial structural schematic diagram of the notching position according to a fifth embodiment of the present invention.

The length and position of the slots of the fifth embodiment is shown in FIG. 9, and the drug-carrying slots 2 are located at the straight rod segment 20 and the transition segments 21, 22 of the stent main supporting wave rod, while extending to the reinforcement ring, but not reaching the center of the reinforcement ring, and the accumulative slot-length covers 75% of the total wave rod length of the main supporting unit rings. The other sizes of the stent are also the same as the first embodiment.

Limit expansion fracture experiment, fatigue test and drug dripping homogenicity test are performed on the above-mentioned embodiments respectively. The experiments show that when stents of the above-mentioned first, second, third, and fourth embodiments are designed as stents with a diameter of 4.0 mm and a length of 18 mm, when a balloon with a diameter of 6.0 mm and a length of 18 mm is used to expand the stents, no fracture happens on the stents when the slot-length is 60%, 64%, 70%, 75% after keeping the pressure at 12 atm for 60 s. However, with the same structural design, when the accumulative slot-length covers 80% and 100% of the wave rod length of the main supporting unit rings, fracture happens when still using the same method to expand the stents. The experiments also show that when doing 10 years fatigue lifetime tests on stents of five different slot-lengths, no deformation and fracture happen to the stents whose slot-length covers 60%, 64%, 70% and 75% of the total wave rod length, while fracture happens to both the stents whose slot-length covers 80% and 100% of the total wave rod length.

When doing drug dripping experiments, when the slot-length is 60%, 64%, 70% and 75%, the drug is distributed homogeneously throughout the whole slots, and during the dripping process, no drug overflows to the interior surface, exterior surface and the side surface outside the stent slots, and the drug-carrying amount meets the requirements. When the slot-length is below 60%, the drug is not distributed homogeneously, and the drug-carrying amount could not meet the requirements for effective cure of lesion, either.

Meanwhile, in the unit waves constituting the stent main supporting wave rod, because the straight rod segment and the transition segment are wider than the reinforcement ring, in the case of a certain width of the slots, when dripping drug to the stent drug-carrying slots, on one hand, the catching capability of the sample application system with respect to the center position of the slots is increased, and on the other hand, when there is not enough time for the drug solvent to evaporate, the drug tends to overflow, at this time because the slot-edge is relatively wide, the adhesion of the drug to the slot-wall is increased, which avoids the drug to overflow to the interior and exterior surfaces and the side surface outside the stent slots, increasing the quality of the stent drug dripping. Preferably, the straight rod segment and the transition segment are 5-15% wider than the reinforcement ring. When the width of straight rod segment is a percent below 5% wider than the width of the reinforcement ring, the drug would overflow.

The unit wave in the intermediate portion of the stent of the present invention is comprised of two types of wave shapes, wherein a design with one type of wave shape having a length shorter than that of the other type of wave shape can increase the support force to pathogenic plaque. Compressed-grasping experiments are performed on the first and third embodiments, after compressed-grasping, no contact is observed between the stent wave rod and the connecting rod, and the balloon was not broken. Preferably, on type of wave shape length is 25-35% shorter than the other type of wave shape length, and when this range is below 25%, when compressed-grasping the stent, the S shaped connecting rod 16 would be in contact with the wave crest of the shorter wave 11, crashing the balloon and causing safety risks; while this range is above 35%, the mesh area of the stent is increased to some extent, and the covering area of metal decreases, the supporting ability to pathogenic plaque decreases.

Therefore, the designs of the slot-length and the structure of the stents of the present invention are reasonable and safe.

The invention claimed is:

1. A coronary artery vascular stent with drug-carrying slots, comprised of a plurality of main supporting unit rings and connecting rods at the proximal, distal and in the intermediate portion of the stent, said main supporting unit ring consists of a plurality of unit waves, the unit waves include wave rods, wherein exterior surfaces of the unit wave rods have drug-carrying slots, characterized in that
the accumulative slot-length of the drug-carrying slots covers 60%-75% of the total wave rod length of the main supporting unit rings, and that the connecting rods have no drug-carrying slots,
each of the unit waves consist of a reinforcement ring, a straight rod segment and a transition segment connecting the reinforcement ring and the straight rod segment,
the straight rod segment and the transition segment are 5-15% wider than the reinforcement ring,
the unit wave in the intermediate portion of the stent is comprised of two types of wave shapes, wherein the wave shape length of on type is shorter than that of the other type, and
the wave shape length of the one type is 25-35% shorter than that of the other type.

2. The vascular stent according to claim 1, characterized in that the accumulative slot-length of the drug-carrying slots covers 64%-70% of the total wave rod length of the main supporting unit rings.

3. The vascular stent according to claim 1, characterized in that the adjacent main supporting unit rings are connected by the connecting rods to form a cylinder-shaped circular stent.

4. The vascular stent according to claim 1, characterized in that the drug-carrying slots are located at the straight rod segment, or at the straight rod segment and the transition segment, or extend to a small segment of the reinforcement ring.

5. The vascular stent according to claim 1, characterized in that the reinforcement ring is a circular arc with a radian larger than 180 degrees.

6. The vascular stent according to claim 1, characterized in that the wave rod exterior surface of each unit wave only has one drug-carrying slot.

7. The vascular stent according to claim 1, characterized in that the drug-carrying slots are strip-shaped.

8. The vascular stent according to claim 1, characterized in that the drug-carrying slots are non-penetrable slots.

9. The vascular stent according to claim 1, characterized in that the drug-carrying slots are made by laser cutting technique.

10. The vascular stent according to claim 1, characterized in that the vascular stent is made of cobalt based alloy, stainless steel or magnesium alloy.

11. A coronary artery vascular stent, comprising:
a plurality of main supporting unit rings; and
connecting rods disposed at proximal, distal and intermediate portions of the stent, characterized in that
said main supporting unit rings include a plurality of unit waves, the unit waves include wave rods,
exterior surfaces of the wave rods have drug-carrying slots, while the connecting rods have no drug-carrying slots, and
an accumulative slot-length of the drug-carrying slots covers 60%-75% of a total wave rod length of the main supporting unit rings,
each of the unit waves includes a reinforcement ring, a straight rod segment and a transition segment connecting the reinforcement ring and the straight rod segment,
the straight rod segment and the transition segment are 5-15% wider than the reinforcement ring,
the unit wave in the intermediate portion of the stent is comprised of two types of wave shapes, wherein the wave shape length of one type is shorter than that of the other type, and
the wave shape length of the one type is 25-35% shorter than that of the other type.

12. The vascular stent according to claim 11, characterized in that the accumulative slot-length of the drug-carrying slots covers 64%-70% of the total wave rod length of the main supporting unit rings.

13. The vascular stent according to claim 11, characterized in that the drug-carrying slots are located in the straight rod segment.

14. The vascular stent according to claim 11, characterized in that the drug-carrying slots are located in the straight rod segment or in the transition segment.

* * * * *

UNITED STATES PATENT AND TRADEMARK OFFICE
CERTIFICATE OF CORRECTION

Page 1 of 1

PATENT NO.         : 9,089,446 B2
APPLICATION NO.    : 13/127548
DATED              : July 28, 2015
INVENTOR(S)        : Li et al.

It is certified that error appears in the above-identified patent and that said Letters Patent is hereby corrected as shown below:

In the claims
Col. 7, claim 1, line 40 reads wave shape length of "on" type is shorter than that of the
Col. 7, claim 1, line 40 should read wave shape length of --one-- type is shorter than that of the Signed and Sealed this
Twenty-second Day of December, 2015

Michelle K. Lee
*Director of the United States Patent and Trademark Office*